United States Patent

Holan et al.

[11] 4,390,715
[45] Jun. 28, 1983

[54] PENTAFLUOROBENZYL ESTERS

[75] Inventors: George Holan, Brighton; David F. O'Keefe, Mt. Waverley, both of Australia

[73] Assignee: Commonwealth Scientific and Industrial Research Organization, Australia

[21] Appl. No.: 282,190

[22] Filed: Jul. 10, 1981

[30] Foreign Application Priority Data

Jul. 18, 1980 [AU] Australia .............................. PE4608

[51] Int. Cl.³ .............................................. C07C 69/76
[52] U.S. Cl. .................................... 424/282; 424/308; 560/102; 560/59; 549/447
[58] Field of Search .................. 560/59, 102; 424/282, 424/308; 260/340.5 R

[56] References Cited

U.S. PATENT DOCUMENTS

| 4,130,656 | 12/1978 | Greuter et al. | 560/102 |
| 4,220,591 | 9/1980 | Holan et al. | 560/59 |
| 4,235,926 | 11/1980 | Holan et al. | 560/102 |
| 4,262,014 | 4/1981 | Holan et al. | 560/59 |

Primary Examiner—Paul J. Killos
Attorney, Agent, or Firm—Bacon & Thomas

[57] ABSTRACT

The (+), (−) and (±) forms of the compounds of the general formula (I)

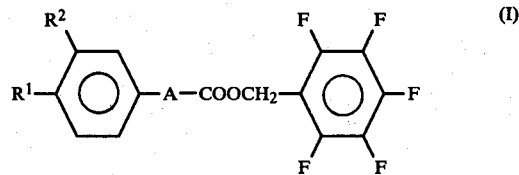

characterized in that
$R^1$ is a halo group; or a lower alkyl, lower alkoxy or lower alkylthio group, each of which may be substituted with one or more halo groups;
$R^2$ is hydrogen or a methyl group; or $R^1$ and $R^2$ together form a methylenedioxy, or a difluoromethylenedioxy group or, with the carbon atoms to which they are attached, an aromatic or heteroaromatic ring; and
A is one of the groups X or Y

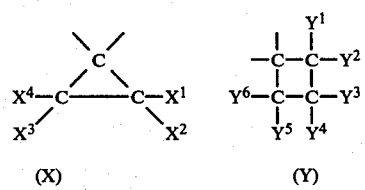

wherein
$X^1$ and $X^2$ are the same or different and each is hydrogen or a fluoro, chloro, bromo or methyl group, with the proviso that if $X^1$ is a fluoro group, then $X^2$ should not be a bromo group; and $X^3$ and $X^4$ are the same or different and each is hydrogen or a fluoro group; and
$Y^1$, $Y^2$, $Y^3$, $Y^4$, $Y^5$ and $Y^6$ are the same or different groups and each is hydrogen or a fluoro, bromo, chloro, or methyl group.
The compounds (I) are insecticidally active.

16 Claims, No Drawings

PENTAFLUOROBENZYL ESTERS

This invention relates to new insecticidal compounds, methods of preparing these compounds and to new insecticidal compositions containing the compounds.

Throughout this specification, where the context permits, the word "insect" is used in its broad common usage and includes spiders, mites, nematodes and other pests which are not classed as insects in the strict biological sense. Thus the term implies reference not only to those small invertebrate animals belonging mostly to the class Insecta, comprising six-legged, usually winged forms, such as beetles, bugs, flies and the like, but also to other allied classes of arthropods whose members are wingless and usually have more than six legs, such as spiders, wood lice and the like, and especially to the order Acaridae which includes the mites and ticks. The words "insecticide" and "insecticidal" are similarly used.

The compounds provided by this invention have the general formula I $$R^2-\text{Ar}(R^1)-A-COOCH_2-C_6F_5 \quad (I)$$

wherein
- $R^1$ is a halo group; or a lower alkyl, lower alkoxy or lower alkylthio group, each of which may be substituted with one or more halo groups;
- $R^2$ is hydrogen or a methyl group; or $R^1$ and $R^2$ together form a methylenedioxy, or a difluoromethylenedioxy group or, with the carbon atoms to which they are attached, an aromatic or heteroaromatic ring; and
- A is one of the groupd X or Y $$\begin{array}{cc}
\underset{X^3}{\overset{X^4}{>}}C-\underset{X^2}{\overset{X^1}{<}}C & \underset{Y^5\ Y^4}{\overset{Y^1}{-}C-\overset{Y^2}{C}-Y^3} \\
(X) & (Y)
\end{array}$$

wherein
- $X^1$ and $X^2$ are the same or different and each is hydrogen or a fluoro, chloro, bromor or methyl group, with the proviso that if $X^1$ is a fluoro group, then $X^2$ should not be a bromo group; and
- $X^3$ and $X^4$ are the same or different and each is hydrogen or a fluoro group; and
- $Y^1, Y^2, Y^3, Y^4, Y^5$ and $Y^6$ are the same or different groups and each is hydrogen or a fluoro, bromo, chloro, or methyl group.

As used herein "halo" means fluoro, chloro or bromo; "lower" implies alkyl groups having from 1 to 4 carbon atoms. Alkyl groups having more than 2 carbon atoms may be straight or branched.

The compounds of Formula I are optically active and can be resolved into their optical isomers by conventional methods. The invention thus includes the individual (+) and (−) isomers of the compounds as well as the racemic (±) forms.

The compounds of the invention show insecticidal activity.

Related prior art compounds disclosed in our Australian Pat. No. 502,950 corresponding to U.S. Pat. No. 4,220,591 and Australian Patent Applications Nos. 42723/78 and 53372/79, corresponding to U.S. Pat. Nos. 4,235,926 and 4,277,490 respectively, are esters of acids of the general formula (II)

$$R^2-\text{Ar}(R^1)-A-COOH \quad (II)$$

(wherein A, $R^1$ and $R^2$ are essentially as defined above (except where $R^1$ and $R^2$ form the difluoromethylenedioxy group or a heteroaromatic system)) with one of the following alcohols:
- 3-phenoxybenzyl alcohol
- 2-benzyl-4-furylmethanol
- α-cyano-3-phenoxybenzyl alcohol
- 3,4-methylenedioxybenzyl alcohol
- α-ethynyl-3-phenoxybenzyl alcohol
- α-cyano-3-(4-chlorophenoxy)benzyl alcohol Australian Patent Application No. 44893/79 (Bayer A. G.) describes insecticidally active pentafluorobenzyl esters of 2,2-dimethyl-3-(substituted vinyl or cycloalkylidenemethyl)cyclopropane carboxylic acids.

These compounds are related to the synthetic pyrethroid type of insecticide such as Permethrin which are 2,2-dimethylcyclopropanes with the large substituents on the 1 and 3 positions of the cyclopropane ring. The compounds of the present invention have both large substituents on the 1 position of the cyclopropane ring. These 1,1-substituted-cyclopropane esters are generally superior in insecticidal activity to the 1,3-substituted-cyclopropane esters of the prior art.

The compounds of the present invention can be prepared
(a) by the reaction of the appropriate acid (formula (II)

$$R^2-\text{Ar}(R^1)-A-COOH \quad (II)$$

(wherein $R^1$, $R^2$ and A are as defined above) with pentafluorobenzyl bromide in an inert solvent and in the presence of a phase transfer catalyst, preferably a crown ether, and a basic alkali metal salt;
(b) by reaction of an alkali metal salt of the acid (II) with pentafluorobenzyl bromide in an aprotic solvent, such as DMF, DMSO or ethylene glycol dimethyl ether;
(c) by reaction of the acid (II) or a suitable reactive derivative thereof, such as the acid chloride, with pentafluorobenzyl alcohol, in an inert solvent and in the presence of a base catalyst, such as pyridine.

All of the above reactions may be performed at atmospheric pressure and at temperatures in the range 0° to 100° C.

Preparations of the acids of formula II are described in our aforementioned Patent and Patent Applications.

The new compounds described herein may be dissolved in a suitable organic solvent, or mixture of solvents, to form solutions or brought into aqueous suspensions by dispersing organic solvent solutions of the compounds in water, to provide useful liquid compositions, which may be incorporated, for example, into aerosol-type dispersions with the usual propellants.

The compounds may also be incorporated in solid compositions which may include inert solid diluents or carriers, to form useful solid compositions. Such compositions may also include other substances such as wetting, dispersing or sticking agents, and may be prepared in granular or other forms to provide slow release of the compounds over an extended period of time. The compounds may be employed in such compositions either as the sole toxic agent or in combination with other insecticides such as pyrethrum, rotenone, or with fungicidal or bactericidal agents, to provide compositions useful for household and agricultural dusts and sprays, textile coating and impregnation, and the like.

In particular, the compounds of the invention may be advantageously combined with other substances which have a synergistic or potentiating action. Generally such substances are of the class of microsomal oxidase inhibitors i.e., they inhibit the detoxification of insecticides in insects produced by the action of oxidative enzymes. Typical substances of this type are the pyrethrin synergists of which the following are examples:

| Common Name | Chemical Name |
|---|---|
| Piperonyl butoxide | α[2-(2-butoxyethoxy)ethoxy]-4,5-methylenedioxy-2-propyl-toluene |
| Piperonyl cyclonene | 3-hexyl-5(3,4-methylenedioxy-phenyl)-2-cyclohexanone |
| "Sesoxane" (Sesamex) | 2-(3,4-methylenedioxy-phen-oxy)-3,6,9-trioxaundecane |
| "Sulfoxide" | 1,2-(methylenedioxy)-4-[2-(octylsulfinyl)propyl]-benzene |
| n-Propyl isome | dipropyl-5,6,7,8-tetrahydro-7-methylnaphtho-[2,3-d],3-dioxole-5,6-dicarboxylate |

("Sesoxane", "Sesamex" and "Sulphoxide" are Registered Trade Marks).

Piperonyl butoxide is particularly useful as a potentiator. The amount of piperonyl butoxide used may vary from 1/1000th to fifty times the weight of the compound I the preferred range being from about 1/100th to an equal part by weight. 'Sesoxane' (made by Shulton Inc., Clifton, N.J., U.S.A.) also is a useful potentiator in similar amounts.

In general, the compositions of the invention will contain from 0.5 to 95% by weight of the active substance, i.e., the compound(s) of formula I and the synergist or potentiator, if used. The broad composition ranges of various possible formulations are as follows:

| Formulation type | Active Substance | Diluents |
|---|---|---|
| Emulsifiable concentrate | 5–95% | 95–5% |
| Wettable Powder | 5–95% | 95–5% |
| Granulate | 1–20% | 99–80% |
| Dust | 1–20% | 99–80% |
| ULV Spray | 50–95% | 5–50% |
| Aerosol | 0.5–30% | 99.5–70% |

Examples of formulations in accordance with the invention are as follows: (parts are by weight):

Dusts

The following substances are used to produce (a) a 5% dust and (b) a 2% dust:

(a)
5 parts of active substance,
95 parts of talcum;

(b)
2 parts of active substance,
1 part of highly dispersed silicic acid,
97 parts of talcum.

The active substance is mixed and ground with the carriers.

Granulate

The following ingredients are used to produce a 5% granulate:

5 parts of active substance,
0.25 part of epichlorohydrin,
0.25 parts of cetyl polyglycol ether,
3.50 parts of polyethylene glycol,
91 parts of kaolin.

The active substance is mixed with epichlorohydrin and dissolved with 6 parts of acetone, the polyethylene glycol and cetyl polyglycol ether are then added. The solution obtained is sprayed onto kaolin and the acetone is evaporated off in vacuo.

Wettable powder

The following constituents are used to produce (a) a 40%, (b) and (c) a 25%, and (d) a 10% wettable powder:

(a)
40 parts of active substance,
5 parts of sodium lignin sulphonate,
1 part of sodium dibutyl-naphthalene sulphonate,
54 parts of silicic acid;

(b)
25 parts of active substance,
4.5 parts of calcium lignin sulphonate,
1.9 parts of chalk/hydroxyethyl cellulose mixture (1:1),
1.5 parts of sodium dibutyl-naphthalene sulphonate,
19.5 parts of silicic acid,
19.5 parts of chalk,
28.1 parts of kaolin;

(c)
25 parts of active substance,
2.5 parts of isooctylphenoxy-polyoxyethylene-ethanol,
1.7 parts of chalk/hydroxyethyl cellulose mixture (1:1),
8.3 parts of sodium aluminium silicate,
16.5 parts of kieselguhr,
46 parts of kaolin;

(d)
10 parts of active substance,
3 parts of a mixture of the sodium salts of saturated fatty alcohol sulphates, 5 parts of naphthalenesulphonic acid/formaldehyde condensate,
82 parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable Concentrates

The following substances are used to produce (a) a 10%, (b) a 25%, and (c) a 50% emulsifiable concentrate:
(a)
10 parts of active substance,
3.4 parts of epoxidised vegetable oil,
3.4 parts of a combination emulsifier consisting of fatty alcohol polyglycol ether and alkylaryl-sulphonate calcium salt,
40 parts of dimethylformamide,
43.2 parts of xylene;
(b)
25 parts of active substance,
2.5 parts of epoxidised vegetable oil,
10 parts of alkylarylsulphonate/fatty alcohol polyglycol ether mixture,
5 parts of dimethylformamide,
57.5 parts of xylene;
(c)
50 parts of active substance,
4.2 parts of tributylphenol-polyglycol ether,
5.8 parts of calcium-dodecylbenzenesulphonate,
20 parts of cyclohexanone,
20 parts of xylene.

Emulsions of the required concentration can be prepared from these concentrates by dilution with water.

Spray

The following constituents are used to produce (a) a 5% spray and (b) a 95% spray;
(a)
5 parts of active substance,
1 part of epichlorohydrin,
94 parts of ligroin (boiling limits 160°–190° C.);
(b)
95 parts of active substance,
5 parts of epichlorohydrin.

The preparation and properties of the compounds of the invention are illustrated by the following specific examples. It should be noted, of course, that these examples are intended to be illustrative of the methods and procedures utilized in preparing the compounds and that they are not intended to be restrictive or to be regarded as embodying the only way in which the compounds can be formed and recovered.

EXAMPLE 1

1(4-Ethoxyphenyl)-2,2,3,3-tetrafluorocyclobutane carboxylic acid 2',3',4',5',6'-pentafluorobenzyl ester To a stirred suspension of powdered anhydrous potassium carbonate (0.5 g, 7.24 mM) in dry benzene (250 ml) was added 18-Crown-6 (0.5 g, 1.89 mM), pentafluorobenzylbromide (1.0 g, 3.83 mM) and 1(4-ethoxyphenyl)-2,2,3,3-tetrafluorocyclobutane carboxylic acid (1.0 g, 3.42 mM). The mixture was stirred at 40°–45° C. for 4 hours then added to ice water. The organic layer was separated, washed with 2 M sodium hydroxide solution and water then dried over anhydrous sodium sulphate. The solution was filtered through a short column of silica gel then the solvent was evaporated and the residue dried at 60° C./0.1 torr for 1 hour to give the ester as a colourless oil 1.54 g (95%). Analysis: Found C 51.09%, H 2.90%, F 36.3%; $C_{20}H_{13}F_9O_3$ requires C 50.86%, H 2.77%, F 36.2%.

EXAMPLE 2

1-(4-Ethoxyphenyl)-2,2-difluorocyclopropane carboxylic acid 2',3',4',5',6'-pentafluorobenzyl ester To a solution of 1-(4-ethoxyphenyl)-2,2-difluorocyclopropane carboxylic acid (0.47 g) in dry benzene (140 ml) was added pentafluorobenzyl bromide (0.60 g), 18-Crown-6 (0.3 g) and anhydrous potassium carbonate (0.3 g). The mixture was stirred at 40°–45° C. for 3 hours then washed with water, dried over anhydrous sodium sulphate and the solvent removed in vacuo. The residue was dissolved in dichloromethane and percolated through a short column of silica gel. The residue after evaporation of solvent was crystallised from diethyl ether/hexane to give the crystals m.p. 68°–9° C.; yield 0.75 g (92%).

Analysis: Found C 54.12%, H 3.05%, F 31.4%, $C_{19}H_{13}F_7O_3$ requires C 54.04%, H 3.10%, F 31.49%.

EXAMPLE 3

R(−)1-(4-Chlorophenyl)-2,2,3,3-tetrafluorocyclobutane carboxylic acid 2',3',4',5',6'-pentafluorobenzyl ester To a stirred suspension of powdered anhydrous potassium carbonate (0.5 g, 7.24 mM) in dry benzene (250 ml) was added 18-Crown-6 (0.5 g, 1.89 mM), pentafluorobenzyl bromide (1.0 g, 3.83 mM) and 1(4-chlorophenyl)-2,2,3,3-tetrafluorocyclobutane carboxylic acid (1.0 g, 3.54 mM). The mixture was stirred at 40°–45° C. for 4 hours then added to ice water. The organic layer was separated, washed with 2 M sodium hydroxide solution and water then dried over anhydrous sodium sulphate. The solution was filtered through a short column of silica gel then the solvent was evaporated and the residue dried at 60° C./0.1 torr for 1 hour to give the ester as a colourless oil 1.54 g (95%). Analysis: Found C 47.02%, H 1.86%, Cl 7.7%, F 37.2%; $C_{18}H_8ClF_9O_2$ requires C 46.73%, H 1.74%, Cl 7.66%, F 37.0%.

EXAMPLE 4

Insecticidal Activity

Insecticidal activity was investigated against blowfly, Lucilia cuprina. The method used was as follows:
(a) The compounds were tested for activity against a dieldrin susceptible strain (BLL) which had been collected before dieldrin usage in the field.

The test compound was applied in acetone solution, 0.5 μl dispensed with a Drummond micropipette to the dorsum of the thorax of 2–3 day old females. Adult flies were fed on water and sugar-only and maintained at 25° C. and 60–70% RH. The mortalities were determined after 24 hours. Moribund flies were regarded as dead. The $LD_{50}$ values, in terms of concentration, were interpolated from a probit/log dose graph using a computer program.

(b) Potentiation

The compound was also tested on the insects described above in conjunction with the potentiator piperonyl butoxide by pretreating each insect with 1 μl of a 2% solution of the potentiator in acetone.

The mortalities were counted at 48 hours after treatment and compared with acetone and acetone/potentiator controls.

The LD$_{50}$ value was determined as described above.

About the same levels of potentiation were obtained when piperonyl butoxide was replaced by an equal amount of 'Sesoxane.'

The insecticidal activity (LD$_{50}$) of the compound of Example 1, measured as described above, the 0.8 μg/female insect. When potentiated with 1 μl of a 2% solution of piperonyl butoxide as a pretreatment on each insect the LD$_{50}$ was 0.01 μg/female insect.

The insecticidal activity (LD$_{50}$) of the compound of Example 2, measured as described above, was 0.038 μg/female insect. When potentiated with piperonyl butoxide as a pretreatment the LD$_{50}$ was 0.014 μg/female insect.

The insecticidal activity (LD$_{50}$ of the compound of Example 3, measured as described above, was 0.05 μg/female insect. When potentiated with piperonyl butoxide as a pretreatment the LD$_{50}$ was 0.01 μg/female insect.

We claim:

1. The (+), (−) and (±) forms of the compounds of the general formula (I)

$$R^1-\underset{R^2}{\underset{|}{\text{Ar}}}-A-COOCH_2-\text{Ar}(F_5) \quad (I)$$

characterised in that

R$^1$ is a halo group; or a lower alkyl, lower alkoxy or lower alkylthio group, each of which may be substituted with one or more halo groups;

R$^2$ is hydrogen or a methyl group; or R$^1$ and R$^2$ together form a methylenedioxy, or a difluoromethylenedioxy group or, with the carbon atoms to which they are attached, an aromatic ring; and A is one of the groups X or Y $$\begin{array}{cc}
X^4-C\underset{X^3}{\overset{\diagdown}{\underset{\diagup}{-}}}C\underset{X^2}{\overset{\diagup}{\underset{\diagdown}{-}}}X^1 & \underset{Y^5\ Y^4}{\underset{|\ \ |}{-C-C-Y^2}} \\
(X) & (Y)
\end{array}$$

wherein

X$^1$ and X$^2$ are the same or different and each is hydrogen or a fluoro, chloro, bromo or methyl group, with the proviso that if X$^1$ is a fluoro group, then X$^2$ should not be a bromo group; and X$^3$ and X$^4$ are the same or different and each is hydrogen or a fluoro group; and Y$^1$, Y$^2$, Y$^3$, Y$^4$, Y$^5$ and Y$^6$ are the same or different groups and each is hydrogen or a fluoro, bromo, chloro, or methyl group.

2. Compounds as claimed in claim 1, characterised in that A is the group Y and Y$^1$, Y$^2$, Y$^3$ and Y$^4$ are each fluoro and Y$^5$ and Y$^6$ are hydrogen.

3. Compounds as claimed in claim 1, characterised in that A is the group X, X$^1$ and X$^2$ are fluoro and X$^3$ and X$^4$ are hydrogen.

4. Compounds as claimed in any one of claims 1 to 3, characterised in that R$^1$ is chloro or ethoxy and R$^2$ is hydrogen.

5. 1(4-Ethoxyphenyl)-2,2,3,3-tetrafluorocyclobutane carboxylic acid 2′,3′,4′,5′,6′-pentafluorobenzyl ester.

6. 1-(4-Ethoxyphenyl)-2,2-difluorocyclopropane carboxylic acid 2′,3′,4′,5′,6′-pentafluorobenzyl ester.

7. R(−)-1(4-Chlorophenyl)-2,2,3,3-tetrafluorocyclobutane carboxylic acid 2′,3′,4′,5′,6′-pentafluorobenzyl ester.

8. Insecticidal compositions, characterised in that they comprise an insecticidally effective amount of one or more of the compounds stated in claim 1, incorporated in a suitable inert liquid or solid carrier.

9. Insecticidal compositions as claimed in claim 8, characterised in that they additionally contain at least one synergistic or potentiating agent of the class of microsomal oxidase inhibitors.

10. Insecticidal compositions as claimed in claim 9, characterised in that the synergist or potentiator is a pyrethrin synergist.

11. Insecticidal compositions as claimed in claim 9, characterised in that the synergist is one of the following:

α[2-(2-butoxyethoxy)ethoxy]-4,5-methylenedioxy-2-propyltoluene;
3-hexyl-5(3,4-methylenedioxyphenyl)-2-cyclohexanone;
2-(3,4-methylenedioxy-phenoxy)-3,6,9-trioxaundecane;
1,2-(methylenedioxy)-4-[2-octylsulfinyl)propyl]-benzene;
dipropyl-5,6,7,8-tetrahydro-7-methylnaphtho-[2,3-di]-1,3-dioxole-5,6-dicarboxylate.

12. Insecticidal compositions as claimed in claim 10 or claim 11, characterised in that the synergist is used in an amount from about 1/1000th to 5 times the weight of the compound I.

13. Insecticidal compositions as claimed in claim 12, characterised in that the synergist is used in an amount from about 1/100th to an equal part by weight per part of the compound I.

14. A method of combatting insect pests, characterised in that an insecticidally effective amount of a compound or composition as claimed in any one of claims 1 to 7, 8 to 13, 15 or 16 is applied to the insects and/or their locus.

15. Insecticidal compositions as claimed in claim 11, characterised in that the synergist is used in an amount from about 1/1000th to 5 times the weight of the compound I.

16. Insecticidal compositions as claimed in claim 15, characterised in that the synergist is used in an amount from about 1/100th to an equal part by weight per part of the compound I.

* * * * *